US011191571B2

United States Patent
Biedermann et al.

(10) Patent No.: US 11,191,571 B2
(45) Date of Patent: Dec. 7, 2021

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Berthold Dannecker, St. Georgen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/181,525

(22) Filed: Feb. 22, 2021

(65) Prior Publication Data
US 2021/0259742 A1 Aug. 26, 2021

Related U.S. Application Data

(60) Provisional application No. 62/981,194, filed on Feb. 25, 2020.

(30) Foreign Application Priority Data

Feb. 25, 2020 (EP) ..................................... 20159292

(51) Int. Cl.
*A61B 17/70* (2006.01)
(52) U.S. Cl.
CPC ...... *A61B 17/7035* (2013.01); *A61B 17/7032* (2013.01)
(58) Field of Classification Search
CPC ............ A61B 17/7032; A61B 17/7035; A61B 17/7037

(Continued)

(56) References Cited

U.S. PATENT DOCUMENTS

| 6,113,601 A | 9/2000 | Tatar |
| 6,248,105 B1 | 6/2001 | Schläpfer et al. |

(Continued)

FOREIGN PATENT DOCUMENTS

| CN | 1254266 A | 5/2000 |
| CN | 101664334 A | 3/2010 |

(Continued)

OTHER PUBLICATIONS

Extended European Search Report for European Application No. EP 10 19 6880, Extended European Search Report dated May 12, 2011 and dated May 20, 2011 (6 pgs.).

(Continued)

*Primary Examiner* — Eduardo C Robert
*Assistant Examiner* — David C Comstock
(74) *Attorney, Agent, or Firm* — Lewis Roca Rothgerber Christie LLP

(57) ABSTRACT

A bone anchoring device includes an anchoring element having a shank and a head, a receiving part configured to pivotably receive the head, and a pressure member defining a head receiving recess for pivotably holding the head and having a portion configured to extend to a side opposite a free end of the head and to exert pressure on the side opposite the free end to clamp the head in the receiving part. The head has a first position indication structure configured to engage a second position indication structure of the pressure member when the shank assumes a first angular position, and to disengage from the second position indication structure when the shank is at an angular position different from the first angular position. The second position indication structure is engageable with the first position indication structure without protruding into a profile defined by the head receiving recess.

22 Claims, 8 Drawing Sheets

(58) Field of Classification Search
USPC .................. 606/266, 267, 268, 270, 308
See application file for complete search history.

(56) References Cited

U.S. PATENT DOCUMENTS

| | | |
|---|---|---|
| 7,001,389 B1 | 2/2006 | Navarro et al. |
| 7,867,258 B2 | 1/2011 | Drewry et al. |
| 9,833,263 B2 | 12/2017 | Chandanson et al. |
| 2004/0267264 A1 | 12/2004 | Konieczynski et al. |
| 2006/0155278 A1 | 7/2006 | Warnick |
| 2006/0173456 A1 | 8/2006 | Hawkes et al. |
| 2007/0055240 A1 | 3/2007 | Matthis et al. |
| 2007/0118117 A1 | 5/2007 | Altarac et al. |
| 2008/0015597 A1 | 1/2008 | Whipple |
| 2008/0045951 A1 | 2/2008 | Fanger et al. |
| 2008/0147121 A1 | 6/2008 | Justis et al. |
| 2008/0269809 A1 | 10/2008 | Garamszegi |
| 2010/0087863 A1 | 4/2010 | Biedermann et al. |
| 2010/0160976 A1 | 6/2010 | Biedermann et al. |
| 2011/0093021 A1 | 4/2011 | Fanger et al. |
| 2011/0098755 A1 | 4/2011 | Jackson et al. |
| 2013/0150852 A1 | 6/2013 | Shluzas et al. |
| 2016/0278832 A1 | 9/2016 | Segawa |
| 2016/0296256 A1* | 10/2016 | Chandanson ...... A61B 17/7037 |
| 2019/0307489 A1* | 10/2019 | Jackson ............ A61B 17/7037 |
| 2020/0069344 A1* | 3/2020 | Capote ............... A61B 17/7034 |
| 2021/0015521 A1 | 1/2021 | Biedermann et al. |

FOREIGN PATENT DOCUMENTS

| | | |
|---|---|---|
| EP | 2 468 198 A1 | 6/2012 |
| EP | 2 606 841 A1 | 6/2013 |
| JP | 2008-526435 A | 7/2008 |
| WO | WO 2006/076422 A2 | 7/2006 |
| WO | WO 2008/112114 A1 | 9/2008 |
| WO | WO 2009/132110 A1 | 10/2009 |

OTHER PUBLICATIONS

Extended European Search Report for European Application No. EP 19187133.4, dated Jan. 27, 2020, 9 pages.
Extended European Search Report for Application No. 20159292.0, dated Oct. 16, 2020, 6 pages.

* cited by examiner

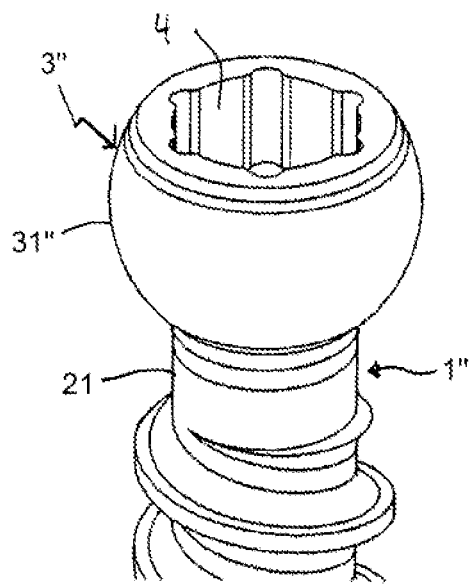
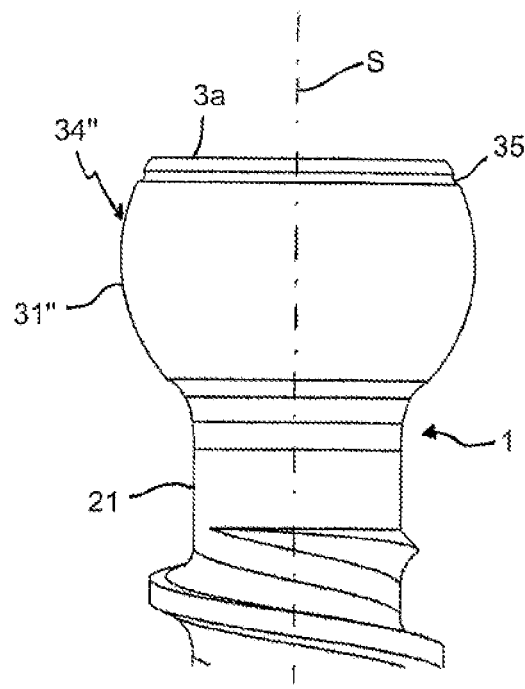
Fig. 17  Fig. 18a
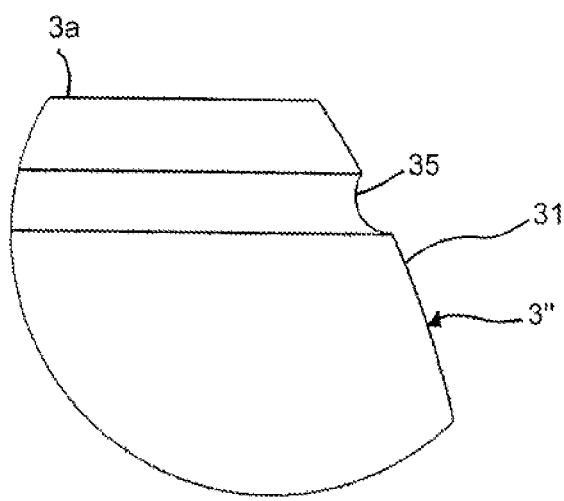
Fig. 18b

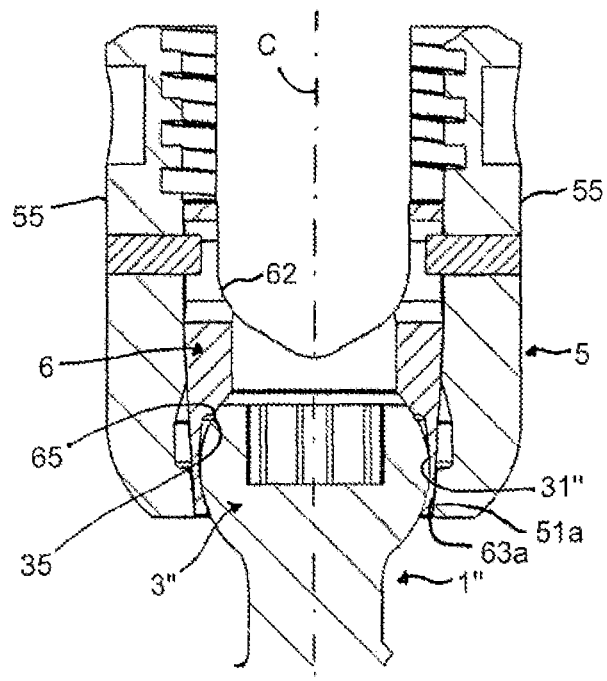 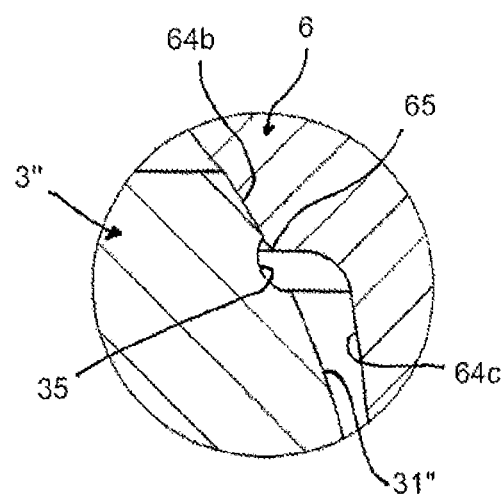
Fig. 19a  Fig. 19b
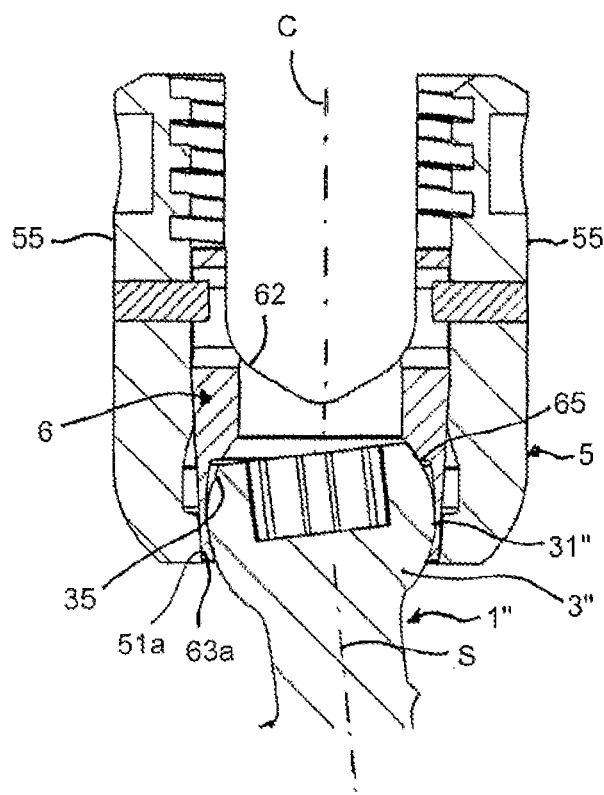 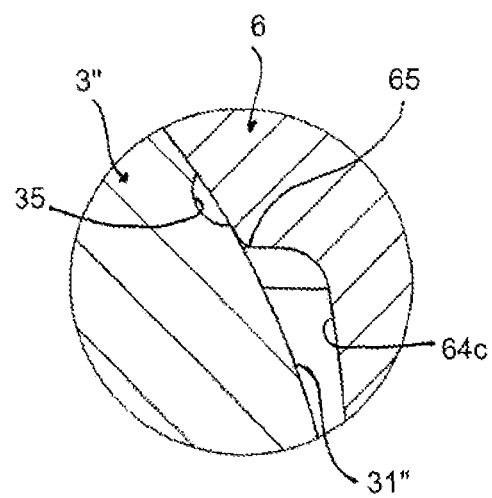
Fig. 20a  Fig. 20b

BONE ANCHORING DEVICE

CROSS-REFERENCE TO RELATED APPLICATION(S)

The present application claims priority to and the benefit of U.S. Provisional Patent Application No. 62/981,194, filed Feb. 25, 2020, the contents of which are hereby incorporated by reference in their entirety, and claims priority from European Patent Application EP 20 159 292.0, filed Feb. 25, 2020, the contents of which are hereby incorporated by reference in their entirety.

BACKGROUND

Field

The application relates to a bone anchoring device of the polyaxial type which indicates a predefined angular position of a bone anchor relative to a receiving part of the bone anchoring device.

Description of Related Art

A bone anchoring device is known from U.S. Pat. No. 9,833,263 B2. The bone anchor assembly described therein includes one or more features for indicating the relative positioning of the receiver member and the shank, for example, in the form of a surface feature included in the head of the bone anchor that interacts with a drag ring to provide tactile or audible feedback when the shank is positioned at a particular orientation with respect to the receiver member. In another embodiment, the head of the bone anchor and a compression cap disposed in the receiver member can each include engagement features that cooperate to allow for selective locking of the orientation of the shank with respect to the receiver member. In the known bone anchor assembly, an interaction between the head and the receiver member is required for indicating a special angular position of the shank. Alternatively, when the orientation indication features are provided only on the head and the compression cap, a position of the compression cap is coupled to a position of the shank relative to the receiver member.

SUMMARY

It is an object of the invention to provide an improved or alternative bone anchoring device that can indicate the position of a shank relative to a receiving part of the bone anchoring device.

According to an embodiment, a bone anchoring device is provided that includes an anchoring element having a shank for anchoring in bone and a head, a receiving part configured to receive the head of the anchoring element in a pivotable manner such that the shank can assume a plurality of angular positions including a predetermined angular position relative to the receiving part, the receiving part having a passage defining a central axis and a pressure member configured to exert pressure onto the head to clamp the head in the receiving part, the pressure member configured to be at least partially arranged in the passage. The head includes a first position indication structure that is configured to engage a second position indication structure of the pressure member to provide an indication of the predetermined angular position of the shank relative to the receiving part. The pressure member may have a head receiving recess to receive at least a portion of the head and a section configured to encompass the head in such a manner that the head is held by friction in the head receiving recess.

In one embodiment, the first position indication structure or the second position indication structure includes a transition between a first curved portion and a second curved portion having different curvatures. When the first position indication structure and the second position indication structure mutually engage and the head is pivoted from one of the angular positions to the predetermined angular position, the transition is passed by the other position indication structure. This produces a feedback. Such a feedback can be received by a user and/or is detectable with a detector.

More specifically, the first and the second curved portions may be surface portions of the head adjoining each other and having different radii. If the second position indication structure provided at the pressure member moves from the surface portion with a smaller radius to the surface portion with a greater radius a feedback is produced.

In another embodiment, the first position indication structure further includes a first flat portion and the second position indication structure further includes a second flat portion configured to engage the first flat portion, and wherein preferably the first and the second flat portions are conical portions. More specifically, the head may include a substantially spherical segment-shaped portion, and a first conical portion may be sandwiched between two spherical sections of the substantially spherical segment-shaped portion. A second conical portion may be provided on the pressure member.

In a still further embodiment, the first position indication structure includes a groove and the second position indication structure includes an edge or protrusion configured to enter at least partially into the groove.

With the bone anchoring device according to embodiments of the invention, the surgical step of aligning the receiving part relative to an inserted shank when the rod and a fixation element are not yet inserted into the receiving part is better facilitated, since a predetermined angular position can be verified. Other angular positions can be adjusted easily since the head is temporarily held by friction relative to the receiving part before locking the head with respect to the receiving part.

The predefined angular position may be a position where the shank and the receiving part are coaxial with respect to each other. This position can be referred to as a "zero position". It may be advantageous for a surgeon to obtain a feedback during alignment of the receiving parts relative to the shanks in-situ when the receiving parts are at the zero position.

With the bone anchoring device according to embodiments of the invention, an interaction to indicate the predefined angular position may be limited to an interaction between only the shank and the pressure member. The receiving part may not be involved when the shank is pivoted and enters the predefined angular position. Hence, the indication of the predefined angular position can be kept substantially independent of the clamping of the head in the receiving part.

The feedback may be a tactile feedback, wherein a user feels with his or her hands when the receiving part has reached the predefined angular position. Moreover, when the receiving part is in the predefined angular position and is moved out thereof, a tactile feedback may be also produced by a resistance that must be overcome in order to move the receiving part away from the predefined angular position.

In some configurations, the feedback to the user may be an audible feedback. Such an audible feedback may be caused by a resilient engagement of the first position indication structure and the second position indication structure.

The first and second position indication structures on the head and the pressure member, respectively, may be provided in both polyaxial bone anchoring devices of the bottom-loading type, i.e., wherein the bone anchoring element is inserted into the receiving part from a bottom end thereof, and polyaxial bone anchoring devices of the top-loading type, i.e., where the bone anchoring element is inserted into the receiving part from the top end thereof.

According to another embodiment, a bone anchoring device is provided that includes an anchoring element having a shank for anchoring in bone and a head, a receiving part configured to receive the head of the anchoring element in a pivotable manner such that the shank can assume a plurality of angular positions including a predetermined angular position relative to the receiving part, the receiving part having a passage defining a central axis, and a pressure member configured to exert pressure onto the head to clamp the head in the receiving part, the pressure member configured to be at least partially arranged in the passage. The head includes a first position indication structure that is configured to engage a second position indication structure of the pressure member to provide an indication of a predetermined angular position of the shank relative to the receiving part. The pressure member has a head receiving recess to receive at least a portion of the head, wherein the head receiving recess includes a spherical surface portion configured to engage a spherical surface portion of the head, and wherein an edge of the spherical surface portion is followed by a cut-out, so that the edge forms the second position indication structure.

BRIEF DESCRIPTION OF THE DRAWINGS

Further features and advantages will become apparent from the detailed description of embodiments by means of the accompanying drawings. In the drawings:

FIG. 9b shows an enlarged view of a detail of FIG. 9a.

FIG. 17 shows a perspective view of a portion of a bone anchoring element according to a third embodiment of the bone anchoring device.

FIG. 18a shows a side view of the bone anchoring element of FIG. 17.

FIG. 18b shows an enlarged portion of FIG. 18a.

FIG. 19a shows a cross-sectional view of the polyaxial bone anchoring device according to the third embodiment, with the bone anchoring element in a zero angle position, the cross-section taken in a plane including the central longitudinal axis of the receiving part and extending through a center of the legs of the receiving part.

FIG. 19b shows an enlarged portion of FIG. 19a.

FIG. 20a shows a cross-sectional view of the polyaxial bone anchoring device of the third embodiment, similar to FIG. 19a, with the bone anchoring element at an angular position different from the zero angle position.

FIG. 20b shows an enlarged portion of FIG. 20a.

DETAILED DESCRIPTION

Figure 1:
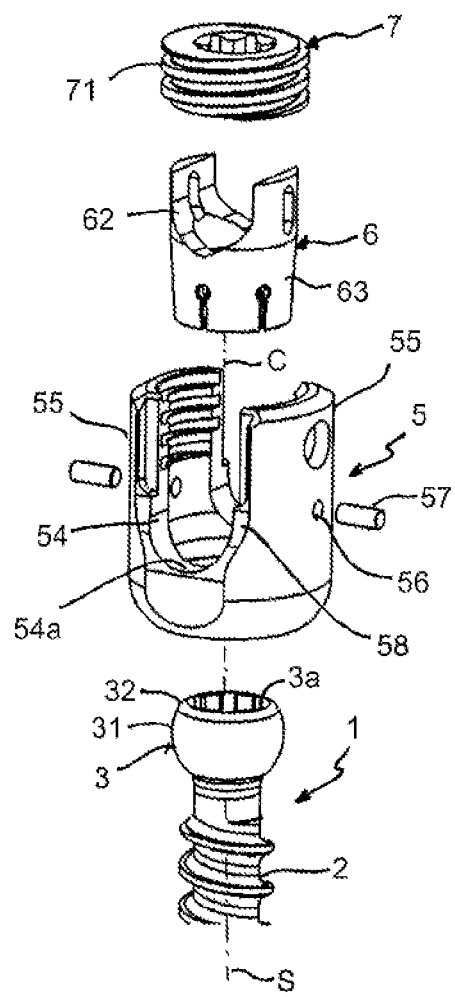
FIG. 1 shows an exploded perspective view of a bone anchoring device according to a first embodiment.
Figure 2:
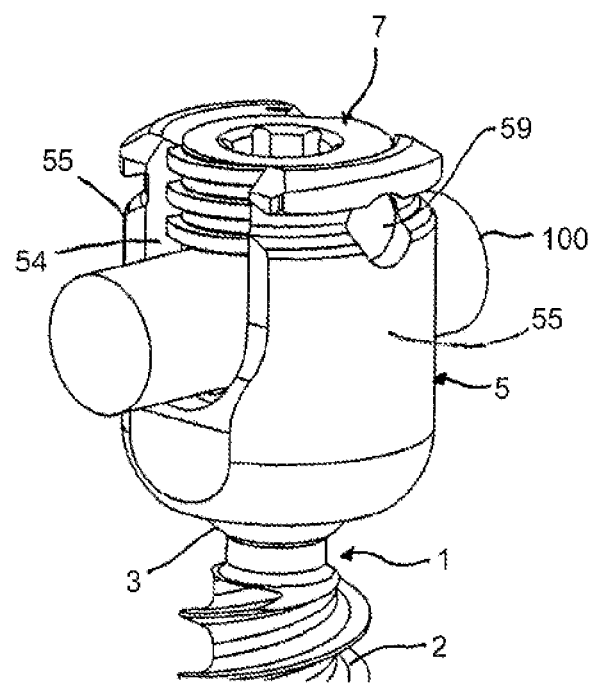
FIG. 2 shows a perspective view of the bone anchoring device of FIG. 1 in an assembled state.
Figure 3:
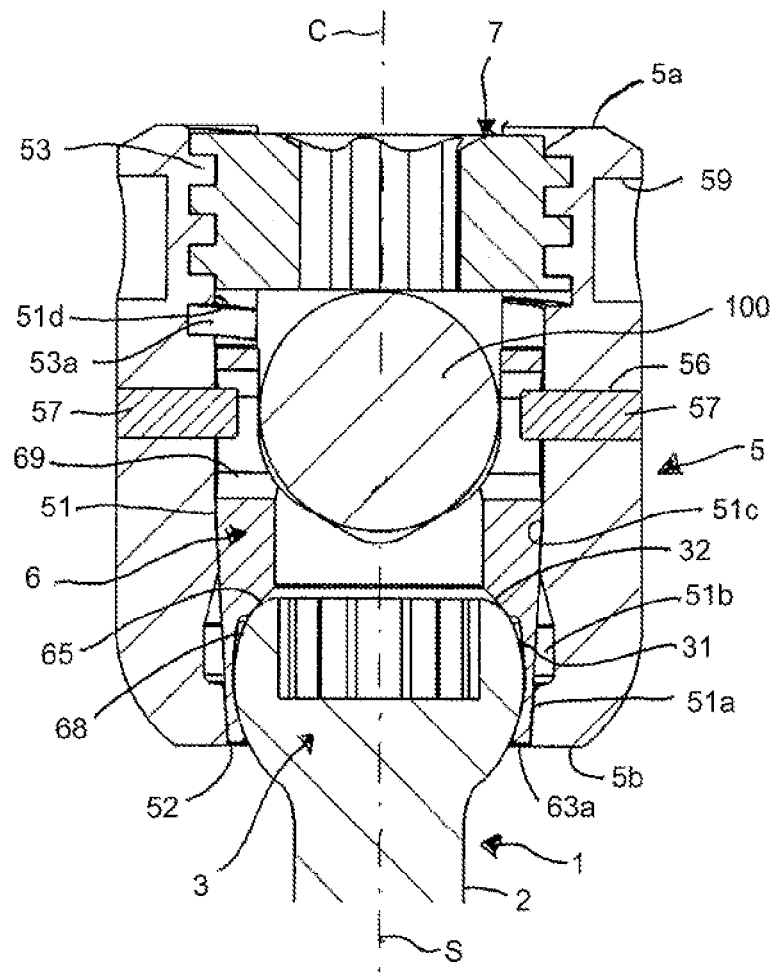
FIG. 3 shows a cross-sectional view of the bone anchoring device of FIGS. 1 and 2, the cross-section taken in a plane including a central longitudinal axis of a receiving part of the bone anchoring device and extending through a center of legs of the receiving part.

A polyaxial bone anchoring device according to a first embodiment, which is generally shown in FIGS. 1 to 3, includes a bone anchoring element 1 in the form of a screw member having a threaded shank 2 and a head 3. A shank axis S is defined by a longitudinal axis or screw axis of the shank 2. On its free end 3a, the head 3 may have a recess 4 for engagement with a tool. The bone anchoring device further includes a receiving part 5 for connecting the bone anchoring element to an elongate stabilization member, such as a rod 100. A pressure member 6 is configured to be arranged in the receiving part on top of the head 3. For securing the rod 100 in the receiving part 5 and to exert pressure onto the pressure member 6, a locking element 7 in the form of, for example, a set screw which cooperates with the receiving part 5 may further be provided.

The receiving part 5 is substantially cylindrical, and has a first or top end 5a, a second or bottom end 5b and a passage 51 extending from the top end 5a towards the bottom end 5b, the passage 51 defining a longitudinal central axis C. The passage 51 forms an opening 52 at the bottom end 5b, which has a width that is greater than a greatest width of the head, so that the head 3 of bone anchoring element 1 is insertable through the bottom end 52. The passage 51 may have several sections with different widths and/or shapes, and is not limited to the exact shape shown in the figures. Adjacent to the opening 52, the passage 51 has a narrowing section 51a which narrows, for example conically, towards the bottom end 5b. The narrowing section 51a cooperates with a portion of the pressure member 6, such that a compressive force is exerted via the pressure member 6 onto an inserted head 3. A widened section 51b follows the narrowing section 51a in a direction towards the top end 5a. The widened section 51b is dimensioned such that a portion of the pressure member 6 can expand therein to permit the head 3 to enter. Further, the passage 51 may have an intermediate section 51c that has a smaller width than the widened section 51b, and permits a portion of the pressure member to slide therein in an axial direction. Finally, adjacent to the top end 5a and the intermediate section 51c, the passage 51 is formed as a threaded bore 51d with a greater inner diameter than that the intermediate section 51c, to permit the insertion of and cooperation with the locking element 7. Threads 53 and 71 of the receiving part 5 and the locking element 7, respectively, may be threads that reduce or eliminate radial forces during tightening of the locking element 7, such as a square thread, for example. At the bottom end of the internal thread 53, a thread runout 53a may be provided. Moreover, as best shown in FIGS. 1 and 2, a substantially U-shaped recess 54 is formed at the top end 5a and extends to a distance therefrom. The substantially U-shaped recess 54 divides the upper portion of the receiving part 5 into two free legs 55, and forms a channel for receiving the rod 100. A longitudinal axis of the substantially U-shaped recess 54 is coaxial with or parallel to a longitudinal axis of a straight rod 100 when the rod is inserted.

At the center of each leg 55 in a circumferential direction and at an axial position above a bottom 54a of the substantially U-shaped recess 54, through-holes 56 extend through each leg 55. The through-holes 56 are configured to receive pins 57, as shown in FIG. 3. The pins 57 may serve for rotationally securing the pressure member 6 in the receiving part 5. Also, the pins 57 may serve for limiting an upward movement of the pressure member 6 within the receiving part 5. Furthermore, cut-outs 58 may be formed on either side of the legs 55, which may contribute to a reduced size of the receiving part 5. A tool engagement portion 59, such as a circumferential groove and/or central recesses can be optionally provided at the legs 55 to allow for engagement of the receiving part 5 by a tool.

Figure 4:
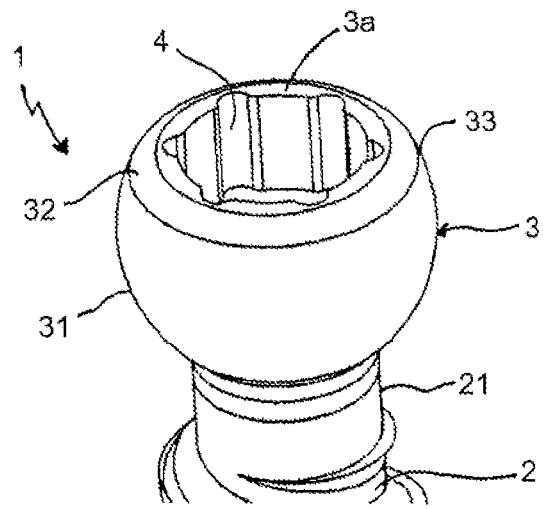
FIG. 4 shows a perspective view from a top of a portion of a bone anchoring element which is part of the bone anchoring device of FIGS. 1 to 3.
Figure 5:
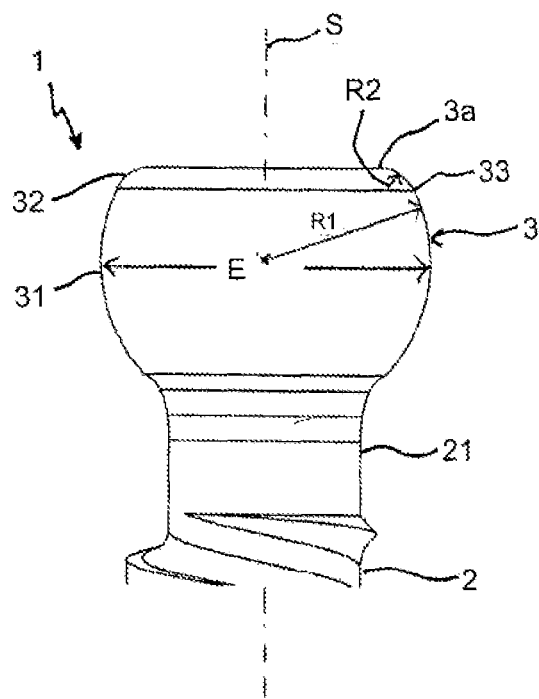
FIG. 5 shows a side view of the portion of the bone anchoring element shown in FIG. 4.
Figure 6:
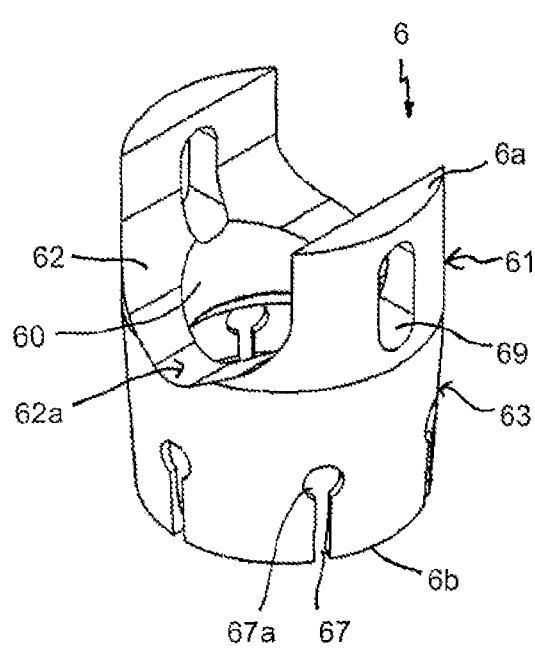
FIG. 6 shows a perspective view from a top of a pressure member of the bone anchoring device according to the first embodiment of FIGS. 1 to 3.
Figure 7:
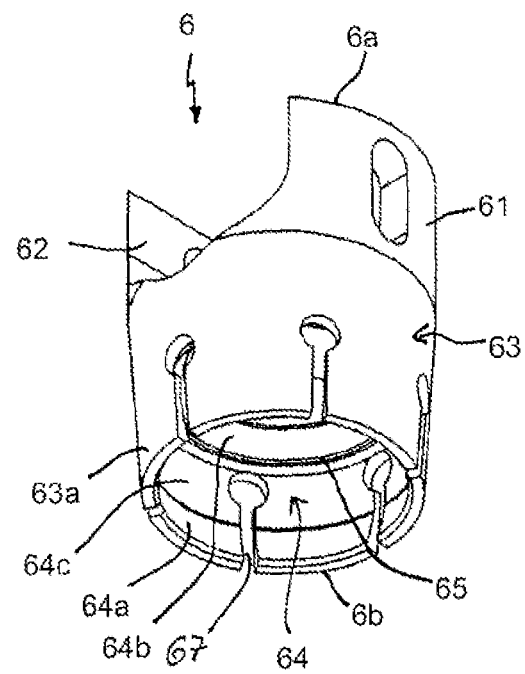
FIG. 7 shows a perspective view from a bottom of the pressure member of FIG. 6.
Figure 8:
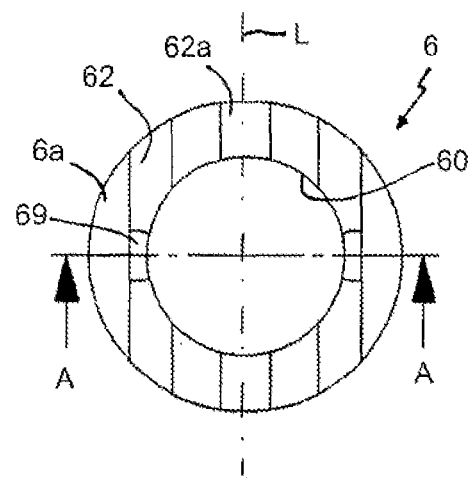
FIG. 8 shows a top view of the pressure member of FIGS. 6 and 7.

Referring additionally to FIGS. 4 and 5, the bone anchoring element 1 will be described in more detail. The head 3 has an overall shape of a segment of a sphere or, in other words, a truncated sphere, which has a size such that it includes a section with a greatest diameter E of the sphere. The segment of the sphere may be arranged in a manner between a free end 3a of the head and a neck portion 21 of the shank 2, such that one end with the smaller outer diameter is closer to the neck portion 21 and the other end with the greater outer diameter is closer to the free end 3a than to the neck portion 21. However, the segment of the sphere can also extend at both sides from the section with the greatest diameter E to the same distance, or may end at or below the greatest diameter E. The neck portion 21 may be substantially thread-free.

More specifically, the head 3 includes at its outer surface a first curved portion 31 and a second curved portion 32. The first curved portion 31 is defined by the spherical segment that forms the overall shape of the head 3 and has a first radius of curvature R1 defined by the radius of the sphere. Further, the first curved portion 31 is located adjacent to or close to the neck portion 21 and includes in the embodiment shown the greatest outer diameter E. The second curved portion 32 may be, for example, substantially toroid segment-shaped and has a second radius of curvature R2 that is smaller than the first radius of curvature R1. The second curved portion 32 is located between the first curved portion 31 and the free end 3a of the head 3. In a section through the center of the head 3 and including the shank axis S, the surface of the first curved portion 31 and the second curved portion 32 form substantially circular arcs. Moreover, the first curved portion 31 and the second curved portion 32 are connected to each other in a manner such that the outer surface of the head 3 is substantially continuous at a transition 33. Hence, there is no substantial step at the transition 33 or in other words, the transition is step-free. The first curved portion 31 and the second curved portion 32 with their transition 33 form a first position indication structure provided on the head 3. It shall be noted that only a part of the entire first curved portion 31 and second curved portion 32 in a region around the transition may form the first position indication structure.

An axial length in the direction of the shank axis S of the second curved portion 32 may be considerably smaller than an axial length of the first curved portion 31. For example, the second curved portion 32 may only have the typical axial length of a bevelled region. The second curved portion may be manufactured, for example, using a turning tool configured to form a radius at an edge of a work piece. It shall be noted that such a first position indication structure including or made up of a transition between a first curvature and a second curvature is relatively easy to manufacture, which contributes to efforts to reduce costs.

The free end portion 3a may be substantially flat. The recess 4 for the tool may have any shape, for example, a polygon shape, a torque-shape, or any other shape to provide a form-fit connection to a tool.

Referring now in addition to FIGS. 6 to 9b, the pressure member 6 will be explained more in detail. The pressure member 6 of this embodiment is a monolithic piece. It has a first or top end 6a and a second or bottom end 6b. Adjacent to the top end 6a, there is an upper portion 61 that may be substantially cylindrical and that has an outer diameter which allows it to move in the axial direction in the passage 51 of the receiving part 5. At the top end 6a, a rod receiving recess 62 is formed that provides a rod support surface. A lower section of the recess 61 may have a substantially V-shaped cross-section with a longitudinal axis extending substantially perpendicular to the cylinder axis of the pressure member 6 which is configured to substantially align with the central axis C of the receiving part 5 when the pressure member is in the receiving part 5. A depth of the recess 62 may be smaller than a diameter of the rod 100. Hence, when the rod 100 rests on the support surface, the rod projects over the top end 6a of the pressure member 6 as shown, for example in FIG. 3. The V-shape of the rod support surface more effectively permits the use of rods with different diameters.

A lower portion 63 of the pressure member 6 has a tapered, preferably conical, outer surface, which is configured to cooperate at its lower region 63a adjacent to the bottom end 6b with the narrowing section 51a of the receiving part. A head receiving recess 64 is formed in the lower portion 63 that extends from the bottom end 6b to a distance from a bottom 62a of the rod receiving recess 62.

Figure 9A:
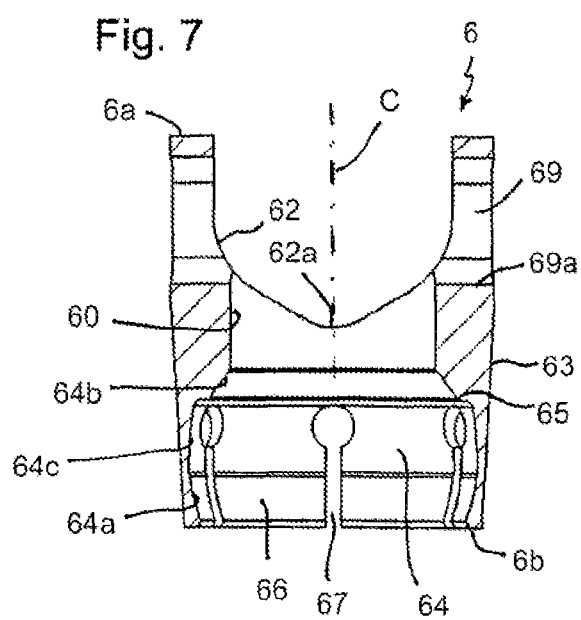
FIG. 9a shows a cross-sectional view of the pressure member of FIGS. 6-8, the cross-section taken along line A-A in FIG. 8.
Figure 9B:
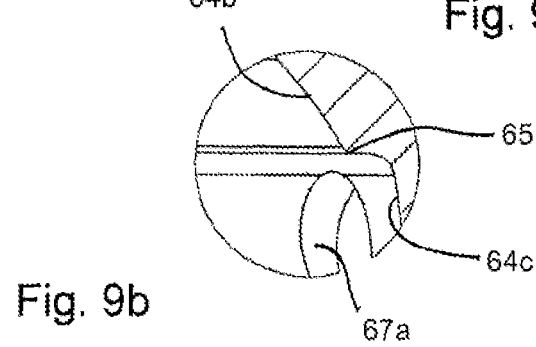

The head receiving recess 64 has a lower section 64a close to the bottom end 6b that has a substantially hollow spherical shape with a radius of the sphere matching that of the first curved portion 31 of the head 3. Furthermore, an uppermost portion 64b of the head receiving recess 64 is also hollow spherically-shaped, for example, with the same radius as the lower portion 64a. By means of this, the lower spherical section 64a and the upper spherical section 64b provide a spherical support for the first curved portion 31 of the head 3, and thus form a seat in which the head 3 can pivot. Between these two spherically-shaped sections 64a, 64b, an intermediate section 64c is provided that forms a cut-out and has a greater inner diameter than the lower end of the upper spherical section 64b. In greater detail, the intermediate widened section 64c widens from the lower end of the upper spherical section 64b, for example, with a substantially flat step, and continues with increasing inner diameter, for example with a conical shape, until it matches the inner diameter of the lower spherical section (FIGS. 9a, 9b). By means of the step, an edge 65 is formed. The edge 65 is preferably rounded. As the edge 65 is defined at a border of the spherical portion, the inner surface of the head receiving recess 64 can be formed substantially free of a separate protrusion that protrudes from the head contacting surface of the spherical portion 64a and 64b into an interior of the recess 64.

In addition, the lower portion 63 of the pressure member includes flexible wall sections 66 that are separated by axial slots 67 open towards the bottom end 6b. To obtain a certain degree of flexibility, the slots 67 may widen towards their closed end 67a. The slots 67 may extend in the axial direction, preferably up to the transition between the intermediate section 64c and the uppermost spherical segment-shaped section 64b.

A size of the head receiving recess 64 and the sections formed therein is such that when the head 3 is inserted, the free end 3a of the head 3 can extend into the upper spherical section 64b. A gap 68 is then formed between the outer surface of the head 3 and the inner surface of the intermediate section 64c of the head receiving recess 64.

Moreover, the size of the head 3 and the lower portion 63 of the pressure member including the head receiving recess 64 is such that the head can be inserted through the bottom end 6b by spreading apart the flexible wall section 66 until the upper portion of the head 3 abuts against or otherwise contacts the edge 65. The connection is similar to a snap-fit connection. When the head 3 is received in the head receiving recess 64, the head is held therein by friction via the flexible wall sections 66 before final locking is effected, for example, with the locking element 7.

The pressure member further includes elongate recesses 69 that are formed in the sidewalls of the rod receiving recess 62. The elongate recesses 69 are oriented with their long side substantially parallel to the central axis C. As shown in FIG. 3, the elongate recesses 69 extend through the entire sidewall and are configured to receive the pins 57. By means of this, when the pressure member 6 is mounted to the receiving part 5, a rotational position of the pressure member 6 can be maintained by the pins 57 that extend into the elongate recesses 69. Furthermore, an upward movement of the pressure member 6 relative to the receiving part towards the first end 5a is limited by an abutment of the pins 57 against the lower end 69a of the recesses 69.

Lastly, the pressure member 6 has a coaxial bore 60 for allowing access to the head 3, more particularly to the recess 4 of the bone anchoring element 1 with a tool.

The parts and portions of the bone anchoring device may be made of any material, preferably however of titanium or stainless steel or any bio-compatible metal or metal alloy or plastic material. For bio-compatible alloys, a NiTi alloy, for example Nitinol, may be used. Other materials that can be used are magnesium or magnesium alloys. Bio-compatible plastic materials that can be used may be, for example, polyether ether ketone (PEEK) or poly-L-lactide acid (PLLA). The parts can be made of the same or of different materials from another.

In use, the bone anchoring element 1 may be inserted first into a prepared hole in bone or in a vertebra, and the receiving part 5 with the pre-assembled pressure member 6 is mounted onto the head 3. Alternatively, the bone anchoring device is pre-assembled in such a manner that the receiving part 5 with the pressure member 6 is already mounted onto the head 3. For mounting, the head 3 is inserted from the lower end 5a of the receiving part while the pressure member 6 is at an uppermost insertion position where the pins 57 abut against the lower end 69a of the elongated recesses 69. Once the head 3 has been inserted, the pressure member 6 is moved downward until the lower outer tapered portion 63a enters into the narrowing section 51a of the receiving part 5 and exerts a compression force onto the head 3. Also, in this condition, the head 3 cannot be removed through the lower opening 52.

As long as the bone anchoring device is not yet finally locked by inserting the rod and fixing it with the locking element 7, the receiving part 5 and the bone anchoring element 1 can be pivoted relative to each other so that the bone anchoring element 1 can assume various angular positions of the shank axis S with respect to the central axis C of the receiving part. Depending on the strength of the frictional clamping of the head 3, any position can be maintained provisionally before locking. This is possible without insertion of the rod and the locking element 7.

Figure 10:
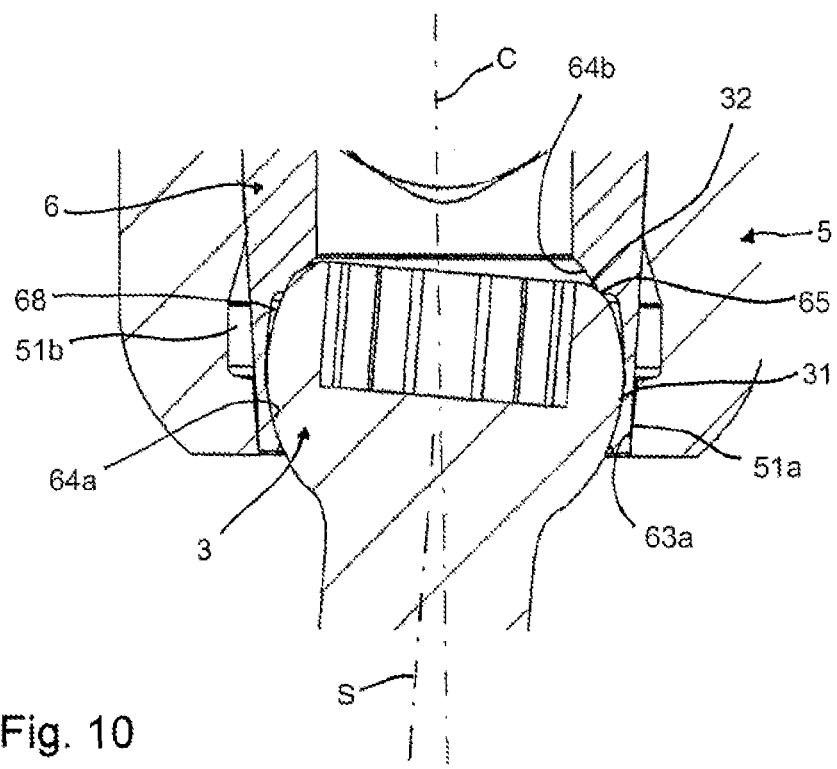
FIG. 10 shows an enlarged cross-sectional view of a portion of the bone anchoring device in an assembled state as shown in FIG. 3, with the bone anchoring element assuming an angle with the central axis of the receiving part which is different from a zero angle (i.e., where axes of the receiving part and bone anchoring element are substantially aligned).
Figure 11:
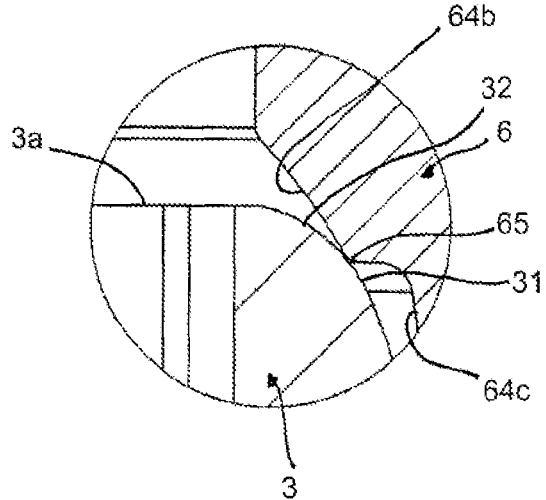
FIG. 11 shows an enlarged cross-sectional view of a portion of the bone anchoring device of FIG. 3 in an assembled state, when the bone anchoring element is in a zero angle position.
Figure 12:
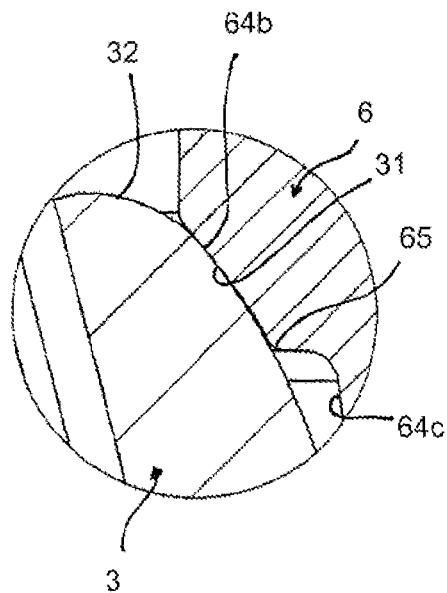
FIG. 12 shows an enlarged cross-sectional view of the bone anchoring device of FIG. 3 when the bone anchoring element is at an angular position different from the zero angle position.
Figure 13:
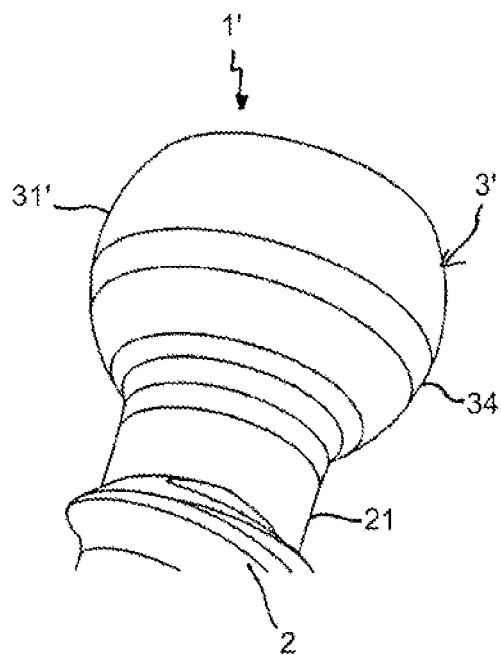
FIG. 13 shows a perspective view of a portion of a bone anchoring element according to a second embodiment of the bone anchoring device.
Figure 14:
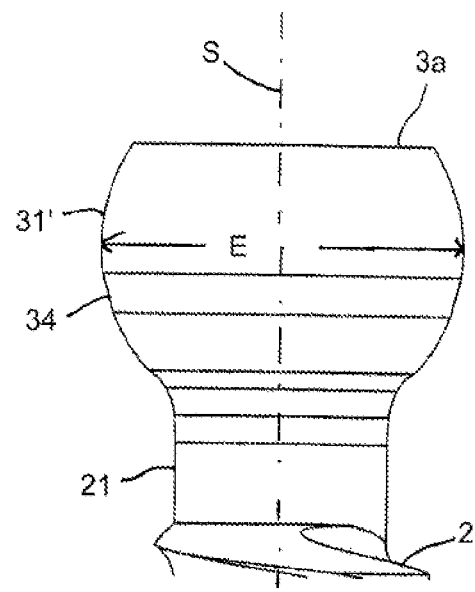
FIG. 14 shows a side view of the bone anchoring element of FIG. 13.

A predetermined position in this embodiment may be the position in which the shank axis S and the central axis C of the receiving part coincide, as shown in FIGS. 3 and 11. In other words, the bone anchoring element assumes a zero angle position with respect to the receiving part 5. A position different from the zero angle position is shown in FIGS. 10 and 12. When the bone anchoring element 1 is moved out of the zero angle position, the edge 65 contacts the second curved portion 32 of the head 3 at a side opposite the side to which the shank is pivoted. When the head 3 is then pivoted relative to the receiving part 5 back towards the zero angle position shown in FIGS. 3 and 11, the edge 65 moves along the outer surface of the head 3 from the second curved portion 32 with the smaller radius back to the first curved portion 31 with the greater radius, thereby passing the transition. During the movement, the pressure member may be slightly expanded until the first curved portion 31 contacts the upper spherical section 64b. The transition from the smaller radius to the greater radius functions in a ramp-like manner and produces a tactile feedback to a user. A user may experience the change in slope until the zero angle position is reached, and/or is left again by pivoting towards another angular position. As the position indication structure provided by the differently curved sections is rotationally symmetrical, the feedback is generated when pivoting in any direction.

Once a suitable angular position is found, the whole construct is locked by inserting the rod and the fixation element 7 and tightening the fixation element 7.

Referring now to FIGS. 13 to 16, a second embodiment of the polyaxial bone anchoring device will be described. The polyaxial bone anchoring device according to the second embodiment differs from the polyaxial bone anchoring device of the first embodiment in the shape of the bone anchoring element and the pressure member. The receiving part is the same as in the first embodiment. Identical or similar parts are indicated with the same reference numerals, and the descriptions thereof will not be repeated. The bone anchoring element 1' has a head 3' which has a spherical segment-shaped portion 31' that may include a section with the greatest diameter E and that joins the neck 21. The spherically-shaped outer surface is interrupted by a conical portion 34 that tapers towards the neck portion 21. The conical portion 34 is located closer to the neck portion 21 than to the free end surface 3a. More specifically, the conical portion 34 is located in a lower portion of the head 3', i.e., is sandwiched between the section with the greatest diameter E and the spherically-shaped portion adjoining the neck portion 21. An axial extension or length of the conical portion 34 may be considerably smaller than the axial extension of the entire spherical segment-shaped portion 31'. The axial length or height may be as large as there is still enough spherical surface for allowing pivoting. Specifically, it may be, for example, less than a third or even less than a quarter of the axial length of the spherical segment-shaped portion 31'.

Figure 15:
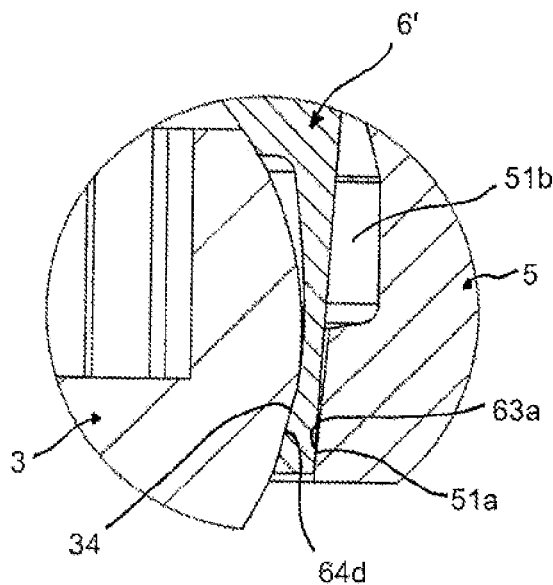
FIG. 15 shows an enlarged cross-sectional view of a portion of the second embodiment of the bone anchoring device with the bone anchoring element in a zero angle position.
Figure 16:
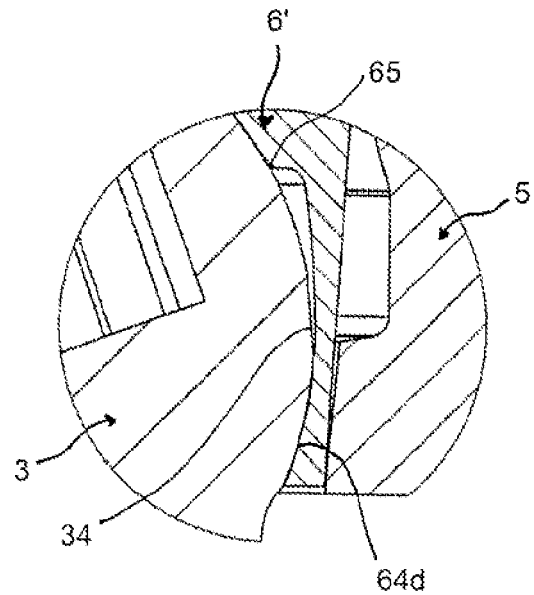
FIG. 16 shows an enlarged cross-sectional view of the portion of the second embodiment of the bone anchoring device shown in FIG. 15, with the bone anchoring element at an angular position different from the zero angle position.

The pressure member 6' is identical to the pressure member of the previous embodiment except that it instead has a counterpart conical section for engaging the conical section 34 of the head 3'. As shown in FIGS. 15 and 16, a conical section 64d is formed within the lower spherical section 64a of the head receiving recess 64. The conical section 64d may have the same cone angle as the conical section 34 of the head 3' and may have the same axial extension or length. However, the axial extension may also, for example, be smaller than that of the conical section 34 of the head 3'. The conical section 64d extends fully circumferentially around the inner wall of the head receiving recess 64 and is at a height such that in the zero angle position, it matches with (i.e., is at substantially the same height as) the conical portion 34 of the head 3'.

In use, when the head 3' is inserted into the pressure member 6', which is in the receiving part 5, and the pressure member is moved downward so that the outer conical section 63a of the pressure member and the narrowing section 51a of the receiving part are engaged to clamp the head, the head is captured in the head receiving recess 64 such that the spherical segment-shaped portion 31' contacts the spherical sections 64a and 64b of the head receiving recess 64 to allow pivoting of the bone anchoring element. When the bone anchoring element 1' is in the zero angle position as depicted in FIG. 15, the conical sections 34 of the head 3' and 64d of the pressure member 6' are engaged. By means of this, the zero angle position is automatically centered. When the bone anchoring element is pivoted to an angular position different from the zero angle position as shown in FIG. 16, the conical sections 34 of the head 3' and 64d of the pressure member are substantially out of engagement. Moving into the zero angle position or out of the zero angle position produces a feedback, preferably a tactile feedback to a user. Hence, the zero angle position can be easily identified.

It shall be noted that the bone anchoring element 1' depicted in FIGS. 13 to 16 does not include the second curved portion 32 close to the free end surface 3a which has a smaller radius in the previous embodiment. However, it is conceivable that the bone anchoring element 1' also has the second curved portion 32 with a smaller radius as in the first embodiment.

Referring to FIGS. 17 to 20b, a third embodiment of the polyaxial bone anchoring device will be described.

The polyaxial bone anchoring device according to the third embodiment differs from the polyaxial bone anchoring device according to the first and second embodiment in the shape of the bone anchoring element, and more specifically in the shape of the head of the bone anchoring element. Parts and portions that are identical or similar to those of the previous embodiments are indicated with the same reference numerals, and the descriptions thereof will not be repeated. The bone anchoring element 1" includes a head 3", which has an overall spherical segment-shaped portion 31" similar to the prior embodiments. The spherical segment-shaped portion 31" may include the section with the greatest diameter E. At a distance from the free end 3a, a groove 35 is formed that extends circumferentially and concentrically around the central axis. The groove 35 may have a rounded inner contour, such as a spherical contour. Moreover, the groove 35 is relatively small and shallow. Specifically, the depth of the groove 35 may be such that it is sufficient to generate a transition between the spherical outer contour of the spherical segment-shaped portion 31" and the groove 35. An axial position of the groove is such that the groove 35 is closer to the free end 3a than to the neck portion 21. It may be, as shown in the figures, at a distance from the free end 3a that is the about same or only slightly greater than a width or height of the groove in the axial direction.

In use, when the head 3" is inserted into the head receiving recess 64 of the pressure member 6, when the pressure member 6 is in the receiving part, and moved downward so that the lower outer conical portion 63a of the pressure member 6 engages the narrowing portion 51a of the receiving part to clamp the head, the head 3" abuts against the upper spherical segment-shaped portion 64b of the pressure member. As shown in FIGS. 19a and 19b, when the bone anchoring element is in the zero angle position, the edge 65 is slightly protruding into the groove 35. hence, the bone anchoring element 1" is slightly held in the zero angle position. When the bone anchoring element 1" is pivoted as shown in FIGS. 20a and 20b, the edge 65 is moved out of the groove 35. This gives a feedback, for example a tactile feedback, to a user. Similarly, when the edge 65 moves into the groove 35, a feedback is also generated. The feedback may be a haptic resistance. Hence, when moving into the zero angle position, a feedback is given to a user who may more easily identify the zero angle position.

It shall be noted that the head may additionally have a conical surface like in the second embodiment and the pressure member also additionally a conical surface as in the second embodiment. Alternatively or in addition, the head may have an additional section with a smaller radius like in the first embodiment.

Further modifications of the embodiments described above are conceivable. The features of one embodiment can be combined with those of other embodiments to provide a variety of further embodiments. The receiving part is not limited to the receiving part of the various embodiments shown. As the interaction is only between the head and the pressure member, any of various other known receiving parts may be used and retrofitted with suitable bone anchoring elements and pressure members that have first and second position indication structures. In addition, the position indication structures are not limited to only being able to indicate the zero angle position. They can also be used to indicate a predetermined position in which the shank assumes an angle different from the zero angle with respect to the receiving part. In such a case, the position indication features may be at other locations and/or may itself be angled or otherwise tilted relative to the shank axis.

While the head is shown to be a spherical head and the pressure member is shown to have a spherical head receiving recess, bone anchoring devices according to embodiments of the invention are also not limited thereto. For example, it is conceivable that the head and the pressure member are shaped so as to permit angulation in one or more distinct planes only.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
   an anchoring element having a shank for anchoring in bone and a head comprising an outer surface having a first curvature and a first position indication surface that deviates from the first curvature;
   a receiving part having a central axis defining a coaxial passage configured to pivotably receive the head of the anchoring element, such that the shank can assume a plurality of angular positions relative to the receiving part; and
   a pressure member movable in the passage, the pressure member comprising an inner surface defining a head receiving recess for pivotably holding the head therein, a second position indication surface that deviates from the inner surface, and a portion configured to extend from a free end of the head past a portion of the head with a greatest diameter to a side of the head opposite the free end to exert pressure on the side of the head opposite the free end to clamp the head in the receiving part;
   wherein the first position indication surface is configured to engage the second position indication surface when the shank assumes a first angular position from among the plurality of angular positions relative to the receiving part, and wherein the first and second position indication surfaces are configured to be disengaged from one another when the shank is at an angular position different from the first angular position relative to the receiving part;
   wherein the second position indication surface is engageable with the first position indication surface without protruding into a profile defined by the head receiving recess.

2. The bone anchoring device of claim 1, wherein the first or the inner surface has a second curvature and the second position indication surface deviates from the second curvature.

3. The bone anchoring device of claim 2, wherein at least one of the first position indication surface or the second position indication surface is curved with a curvature different from the first curvature or the second curvature, respectively.

4. The bone anchoring device of claim 1, wherein the first position indication surface further comprises a transition into the first curvature.

5. The bone anchoring device of claim 1, wherein at least one of a transition between the first curvature and the first position indication surface or a transition between the inner surface and the second position indication surface is continuous.

6. The bone anchoring device of claim 1, wherein a transition is formed between the first curvature and the first position indication surface or between the inner surface and the second position indication surface, and wherein the other one of the first or second position indication surfaces comprises an edge configured to pass the transition.

7. The bone anchoring device of claim 1, wherein the head receiving recess has at least two similarly curved portions that are separated axially from one another by a third portion that deviates from the curvature of the two similarly curved portions.

8. The bone anchoring device of claim 1, wherein the head receiving recess is configured to hold an inserted head by friction prior to locking.

9. The bone anchoring device of claim 1, wherein at least one of the first or second position indication surfaces is formed by a groove.

10. The bone anchoring device of claim 1, wherein the first position indication surface is formed by a first flat portion and the second position indication surface is formed by a second flat portion engageable with the first flat portion.

11. The bone anchoring device of claim 10, wherein at least one of the first or second flat portions is conical.

12. The bone anchoring device of claim 1, wherein at least one of the first or second position indication surfaces is rotationally symmetrical.

13. The bone anchoring device of claim 1, wherein the receiving part has a first end and a second end, a recess for receiving a rod at the first end, and an opening at the second end, wherein the head is insertable through the opening into the receiving part.

14. A bone anchoring device comprising:
   an anchoring element having a shank for anchoring in bone and a head comprising an outer surface having a first curvature and a first position indication surface that deviates from the first curvature without forming a groove on the outer surface;
   a receiving part having a central axis defining a coaxial passage configured to pivotably receive the head of the anchoring element, such that the shank can assume a plurality of angular positions relative to the receiving part; and
   a pressure member movable in the passage to exert pressure on the head to clamp the head in the receiving part, the pressure member comprising an inner surface and a second position indication surface that deviates from the inner surface;
   wherein the first position indication surface is configured to engage the second position indication surface when the shank assumes a first angular position from among the plurality of angular positions relative to the receiving part, and wherein the first and second position indication surfaces are configured to be disengaged from one another when the shank is at an angular position different from the first angular position relative to the receiving part.

15. The bone anchoring device of claim 14, wherein the first position indication surface comprises a first conical portion.

16. The bone anchoring device of claim 15, wherein the first conical portion is sandwiched between two spherical segment-shaped sections of the head.

17. The bone anchoring device of claim 15, wherein the first conical portion is closer axially to the shank than it is to a free end of the head.

18. The bone anchoring device of claim 15, wherein the second position indication surface comprises a second conical portion engageable with the first conical portion.

19. The bone anchoring device of claim 14, wherein the first position indication surface is at or near a free end of the head and comprises a transition into the first curvature.

20. A bone anchoring device comprising:
- an anchoring element having a shank for anchoring in bone and a head comprising an outer surface having a first curvature and a first position indication surface that deviates from the first curvature;
- a receiving part having a central axis defining a coaxial passage configured to pivotably receive the head of the anchoring element, such that the shank can assume a plurality of angular positions relative to the receiving part; and
- a pressure member movable in the passage to exert pressure on the head to clamp the head in the receiving part, the pressure member comprising an inner surface defining a spherical segment-shaped head receiving recess for pivotably holding the head therein and a second position indication surface that deviates from the spherical segment-shaped head receiving recess;
- wherein the first position indication surface is configured to engage the second position indication surface when the shank assumes a first angular position from among the plurality of angular positions relative to the receiving part, and wherein the first and second position indication surfaces are configured to be disengaged from one another when the shank is at an angular position different from the first angular position relative to the receiving part;
- wherein the second position indication surface is engageable with the first position indication surface without protruding into a spherical profile defined by the spherical segment-shaped head receiving recess.

21. The bone anchoring device of claim 20, wherein the first position indication surface further comprises a transition into the first curvature.

22. The bone anchoring device of claim 20, wherein the first position indication surface is formed by a groove on an outer surface of the head.

* * * * *

UNITED STATES PATENT AND TRADEMARK OFFICE
CERTIFICATE OF CORRECTION

| | | |
|---|---|---|
| PATENT NO. | : 11,191,571 B2 | Page 1 of 1 |
| APPLICATION NO. | : 17/181525 | |
| DATED | : December 7, 2021 | |
| INVENTOR(S) | : Lutz Biedermann et al. | |

It is certified that error appears in the above-identified patent and that said Letters Patent is hereby corrected as shown below:

In the Claims

Column 11, Lines 54-55, Claim 2    Delete "the first or the",
Insert -- the --

Signed and Sealed this
Third Day of January, 2023

Katherine Kelly Vidal
*Director of the United States Patent and Trademark Office*